(12) United States Patent
Mansfield (10) Patent No.: US 12,377,234 B2
(45) Date of Patent: *Aug. 5, 2025

(54) ACOUSTIC GUIDED SUCTION SYSTEMS, DEVICES, AND METHODS

(71) Applicant: Covidien LP, Mansfield, MA (US)

(72) Inventor: Jeffrey Mansfield, Carmel, IN (US)

(73) Assignee: Covidien LP, Mansfield, MA (US)

( * ) Notice: Subject to any disclaimer, the term of this patent is extended or adjusted under 35 U.S.C. 154(b) by 243 days.

This patent is subject to a terminal disclaimer.

(21) Appl. No.: 17/713,801

(22) Filed: Apr. 5, 2022

(65) Prior Publication Data

US 2022/0226591 A1 Jul. 21, 2022

Related U.S. Application Data

(63) Continuation of application No. 16/054,734, filed on Aug. 3, 2018, now Pat. No. 11,324,906.

(Continued)

(51) Int. Cl.
*A61M 16/04* (2006.01)
*A61M 16/00* (2006.01)

(52) U.S. Cl.
CPC ...... *A61M 16/0463* (2013.01); *A61M 16/024* (2017.08); *A61M 16/0477* (2014.02);
(Continued)

(58) Field of Classification Search
CPC ............ A61M 16/0463; A61M 16/024; A61M 16/0477; A61M 16/0006; A61M 2016/0027; A61M 2205/3375; A61M 2205/502; A61M 2209/10; A61M 2230/005; A61B 5/746; A61B 5/0051; A61B 5/08; A61B 5/6852; A61B 8/12; A61B 8/445

See application file for complete search history.

(56) References Cited

U.S. PATENT DOCUMENTS 2,209,944 A 7/1940 Walker
4,207,874 A 6/1980 Choy
(Continued)

FOREIGN PATENT DOCUMENTS

EP 1166813 1/2002
WO 2009149351 12/2009
(Continued)

OTHER PUBLICATIONS

Nacheli, Gustavo Cumbo, et aL "Novel device (AirWave) to access endotracheal tube migration: A pilot study" Journal of Critical Care. 2013, 535.e1-535.e8, 28, Elsevier Inc.
(Continued)

*Primary Examiner* — Kendra D Carter
*Assistant Examiner* — Arielle Wolff (57) ABSTRACT

A method for guiding suction of an obstruction may comprise emitting sound waves from a sound generator into a tube, detecting returning acoustic reflections with at least one sound receiver, analyzing, using a processor, timings and amplitudes of the returning acoustic reflections to determine a location and size of an obstruction within the tube and a location of a tip of a suction catheter, and guiding the suction catheter to the obstruction.

20 Claims, 9 Drawing Sheets

Related U.S. Application Data (60) Provisional application No. 62/541,491, filed on Aug. 4, 2017.

(52) U.S. Cl.
CPC .. *A61M 16/0006* (2014.02); *A61M 2016/0027* (2013.01); *A61M 2205/3375* (2013.01); *A61M 2205/502* (2013.01); *A61M 2209/10* (2013.01); *A61M 2230/005* (2013.01)

(56) References Cited

U.S. PATENT DOCUMENTS

| | | | |
|---|---|---|---|
| 4,344,436 | A | 8/1982 | Kubota |
| 4,501,273 | A | 2/1985 | McGinnis |
| 4,630,606 | A | 12/1986 | Weerda |
| 4,697,593 | A | 10/1987 | Evans |
| 4,700,396 | A | 10/1987 | Bolin |
| 5,445,144 | A * | 8/1995 | Wodicka ............ A61M 16/202 |
| | | | 128/207.14 |
| 5,445,244 | A | 8/1995 | Ketonen |
| 5,575,310 | A | 11/1996 | Kamen |
| 5,655,518 | A | 8/1997 | Burden |
| 5,666,960 | A | 9/1997 | Fredberg |
| 5,823,965 | A | 10/1998 | Rasmussen |
| 5,853,005 | A | 12/1998 | Scanlon |
| 6,257,234 | B1 | 7/2001 | Sun |
| 6,390,091 | B1 | 5/2002 | Banner |
| 6,443,907 | B1 | 9/2002 | Mansy |
| 6,629,527 | B1 | 10/2003 | Estes |
| 6,705,319 | B1 | 3/2004 | Wodicka |
| 6,761,693 | B1 | 7/2004 | Rasmussen |
| 7,347,824 | B2 | 3/2008 | Wilkinson et al. |
| 7,691,070 | B2 | 4/2010 | Comanducci |
| 7,708,697 | B2 | 5/2010 | Wilkinson et al. |
| 7,850,618 | B2 | 12/2010 | Wilkinson et al. |
| 7,891,354 | B2 | 2/2011 | Farbarik |
| 8,038,629 | B2 | 10/2011 | Solanki |
| 8,152,751 | B2 | 4/2012 | Roger |
| 8,280,489 | B2 | 10/2012 | Li |
| 8,371,303 | B2 | 2/2013 | Schaner |
| 8,394,031 | B2 | 3/2013 | Mansy |
| 8,424,529 | B2 | 4/2013 | Efrati |
| 8,522,787 | B2 | 9/2013 | Lin |
| 8,608,658 | B2 | 12/2013 | Burbank |
| 8,611,984 | B2 | 12/2013 | Greenburg |
| 8,764,725 | B2 | 7/2014 | Averbuch |
| 8,844,534 | B2 | 9/2014 | Behlmaier |
| 8,905,029 | B2 | 12/2014 | Colburn |
| 9,364,180 | B2 | 6/2016 | Armitstead |
| 9,498,590 | B2 | 11/2016 | Mansfield |
| 9,707,363 | B2 | 7/2017 | Mansfield |
| 10,780,238 | B2 | 9/2020 | Efrati et al. |
| 11,324,906 | B2 * | 5/2022 | Mansfield ............ A61B 5/0051 |
| 2001/0004893 | A1 | 6/2001 | Biondi |
| 2002/0016610 | A1 | 2/2002 | Hovanes |
| 2003/0034035 | A1 | 2/2003 | Raphael |
| 2005/0005935 | A1 | 1/2005 | Gradon |
| 2006/0070623 | A1 | 4/2006 | Wilkinson |
| 2006/0070624 | A1 | 4/2006 | Kane |
| 2006/0081255 | A1 | 4/2006 | Miller |
| 2006/0107962 | A1 | 5/2006 | Ward |
| 2007/0137652 | A1 | 6/2007 | Qureshi |
| 2007/0257788 | A1 | 11/2007 | Carlson |
| 2008/0078248 | A1 | 4/2008 | Farbarik |
| 2008/0078390 | A1 | 4/2008 | Milne |
| 2009/0025728 | A1 | 1/2009 | Aljuri |
| 2009/0082676 | A1 | 3/2009 | Bennison |
| 2009/0099479 | A1 | 4/2009 | Solanki |
| 2009/0120439 | A1 | 5/2009 | Goebel |
| 2009/0187164 | A1 | 7/2009 | Rowe |
| 2009/0229605 | A1 | 9/2009 | Efrati |
| 2009/0229611 | A1 | 9/2009 | Martin |
| 2009/0301601 | A1 | 12/2009 | Enerson |
| 2009/0318805 | A1 | 12/2009 | Raphael |
| 2010/0252048 | A1 | 10/2010 | Young |
| 2010/0261996 | A1 | 10/2010 | Li |
| 2011/0030694 | A1 | 2/2011 | Schaner |
| 2011/0087123 | A9 | 4/2011 | Choncholas |
| 2011/0154241 | A1 | 6/2011 | Skidmore |
| 2011/0197885 | A1 | 8/2011 | Wondka |
| 2011/0197888 | A1 | 8/2011 | Deutsch |
| 2011/0313689 | A1 * | 12/2011 | Holley ............... A61M 16/026 |
| | | | 702/56 |
| 2012/0132211 | A1 | 5/2012 | Halperin |
| 2012/0232411 | A1 | 9/2012 | Brunner |
| 2012/0259208 | A1 | 10/2012 | Bloom |
| 2013/0098363 | A1 | 4/2013 | Forte |
| 2013/0228171 | A1 | 9/2013 | Mansfield |
| 2013/0255691 | A1 * | 10/2013 | Mansfield ............ A61M 16/04 |
| | | | 128/207.14 |
| 2013/0281885 | A1 | 10/2013 | Rowbottom |
| 2014/0051989 | A1 | 2/2014 | McGowan |
| 2014/0058253 | A1 | 2/2014 | Prough |
| 2014/0150782 | A1 | 6/2014 | Vazaies et al. |
| 2014/0155720 | A1 | 6/2014 | Stanislaus |
| 2014/0249428 | A1 | 9/2014 | Ingold, Jr. |
| 2014/0366874 | A1 | 12/2014 | Deutsch |
| 2016/0045698 | A1 * | 2/2016 | Chaturvedi ....... A61M 16/0445 |
| | | | 128/204.21 |
| 2016/0279366 | A1 | 9/2016 | Mansfield |
| 2017/0043110 | A1 | 2/2017 | Mansfield |
| 2017/0281887 | A1 | 10/2017 | Mansfield |
| 2017/0340522 | A1 | 11/2017 | Mansfield |
| 2019/0105113 | A1 * | 4/2019 | Popovic ............... A61B 1/0016 |
| 2020/0237977 | A1 | 7/2020 | Panotopoulos |
| 2021/0316094 | A1 | 10/2021 | Kim et al. |

FOREIGN PATENT DOCUMENTS

| | | |
|---|---|---|
| WO | 2010141415 | 12/2010 |
| WO | 2013134166 | 9/2013 |
| WO | 2013149138 | 10/2013 |
| WO | 2016154607 | 9/2016 |

OTHER PUBLICATIONS

Extended European Search Report for European Appl. No.—18841702.6 (PCTiUS20•18045258) mailed May 6, 202•1.

PCT International Search Report and Written Opinion for International Appl. No. PCT/US2018/045258 mailed Oct. 16, 2018.

Boque, et al., Endotracheal tube intraluminal diameter narrowing after mechanical ventilation: use of acoustic reflectometry, Springer-Verlarg, Intensive Care Med, 2004, 30:2204-09.

Schumann, et al., Detection of partial endotracheal tube obstruction by forced pressure oscillations, Respiratory Physiology & Neurobiology 155 (2007), 227-233.

Extended European search report and opinion dated Nov. 17, 2015 for EP Application No. 13770312.0.

Fiastro, et al., Pressure Support Compensation for Inspiratory Work due to Endotracheal Tubes and Demand Continuous Positive Airway Pressure, Chest, Mar. 1988, 93(3):499-505.

International Preliminary Report on Patentability written opinion dated Jul. 11, 2013 for PCT Application No. 2013034599.

International Preliminary Report on Patentability written opinion, International search report and written opinion dated Jun. 24, 2016 for PCT Application No. US-2016024380.

International search report and written opinion dated Jul. 9, 2013 for PCT Application US-2013028957.

International search report and written opinion dated Aug. 10, 2017 for PCT Application No. US-2017035299.

* cited by examiner

ACOUSTIC GUIDED SUCTION SYSTEMS, DEVICES, AND METHODS

CROSS-REFERENCE

This application is a continuation of U.S. application Ser. No. 16/054,734, filed Aug. 3, 2018, which claims the benefit of U.S. Provisional Application No. 62/541,491, filed Aug. 4, 2017, which applications are incorporated herein by reference in their entireties.

This application is related to the following patent applications: application Ser. No. 13/853,252, filed Mar. 29, 2013, now U.S. Pat. No. 9,707,363, the entirety of which is incorporated herein by reference.

BACKGROUND OF THE INVENTION

The present disclosure is generally related to a system and method for use of acoustic reflectometry information for locating and removing obstructions from ventilation systems, such as from within an endotracheal tube.

When a hospital patient is unable to breathe on his own, the patient is connected to a mechanical ventilation device. The patient is first intubated, a procedure in which an endotracheal tube (also called an artificial airway, endotracheal tube, or ETT), is inserted through the nose or mouth into the trachea (wind pipe). The tube is then connected to a mechanical ventilation device, which forces air into the lungs.

Each year, approximately 60 million intubations requiring endotracheal tubes are performed worldwide. Assuring proper placement of the endotracheal tube within the trachea and assuring that it has not moved or become obstructed are significant clinical problems. Failure to correct a misplaced or clogged endotracheal tube can lead to serious complications to the patient, most notably conditions consistent with lack of oxygen such as brain damage or death.

There are known in the art devices that provide direct, precise, real-time monitoring of endotracheal tube (ETT) position and obstructions. Systems and methods for doing this are disclosed in U.S. Pat. Nos. 5,445,144 and 6,705,319 to Wodicka et al. One such commercially available system is the SonarMed® AirWave™ system (available from SonarMed, Inc., 12220 North Meridian Street, Suite 150, Carmel, IN 46032).

Complications with endotracheal tubes include endotracheal tube obstruction wherein lung secretions or other substances block the tube, the tube kinks in the patient's upper airway, or the patient bites excessively on the tube.

SUMMARY

Current acoustic reflectometry systems are deficient in that they cannot and do not provide feedback, such as real-time feedback of the suctioning process by which obstructions within the ETT are removed. Nor do they provide automated identification and suctioning of obstructions within the ETT.

Accordingly, disclosed herein are systems, apparatus, and methods for acoustic guided suction and removal of obstructions from within a tube, such as an ETT.

A method for guiding suction of an obstruction is disclosed. The method may include emitting sound waves from a sound generator into a tube, detecting returning acoustic reflections with at least one sound receiver, analyzing, using a processor, timings and amplitudes of the returning acoustic reflections to determine a location and size of an obstruction within the tube and a location of a tip of a suction catheter, and guiding the suction catheter to the obstruction.

The method may also include fluidically coupling the suction catheter to a vacuum source and removing at least a portion of the obstruction by suctioning the obstruction. The method may also include withdrawing the suction catheter from the tube and analyzing, using a processor, timings and amplitudes of the second returning acoustic reflections to determine whether the obstruction has been removed.

In some embodiments, the method may also include repeating the guiding, fluidically coupling, and removing, steps if the obstruction was determined to not have been removed.

The method may further include indicating that the suction catheter tip is at the obstruction. Guiding may include indicating a relative position of the obstruction and the catheter tube on a display.

The method may include sending the location and degree of obstruction to a suction controller, wherein the suction controller advances the suction catheter to the obstruction.

The method may include determining the suction catheter tip is at the obstruction and indicating that suction may begin when the suction catheter tip is determined to be at the obstruction.

The method may also include analyzing, using a processor, timings and amplitudes of the returning acoustic reflections over a plurality of quiet periods to determine an increase in tube resistance and indicating a recommendation of suctioning based on the increase in tube resistance.

The method may also include sending the location and degree of obstruction to a suction controller, wherein the suction controller advances the suction catheter to the obstruction. The method may include determining by using at least one microphone to detect suction sounds from the suction tube, a duration of suctioning.

A system for guiding suction of an obstruction is also disclosed. The system may include a sound generator to emit sound waves into a tube, at least one sound receiver to detect returning acoustic reflections, and a reflectometry device having at least one processor and a memory that is accessible to the processor for analyzing timings and amplitudes of the returning acoustic reflections to determine a location and size of an obstruction within the tube and the location of a tip of a suction catheter and guiding the suction catheter to the obstruction The system may also include a display and guiding the suction catheter to the obstruction may include displaying relative positions of the suction catheter and the obstruction. The reflectometry device may further causes fluidic coupling of the suction catheter to a vacuum source.

The system may also include a suction controller configured to advance and withdrawing the suction catheter from the tube.

The reflectometry device may be configured to indicate that the suction catheter tip is at the obstruction when the analysis of the timings and amplitudes of the returning acoustic reflections to indicate that the location of the tip of the suction catheter is at the location of the obstruction.

The guiding may include indicating a relative position of the obstruction and the catheter tube on a display. The reflectometry device may be configured to send the location and degree of obstruction to a suction controller and the suction controller is configured to advance the suction catheter to the obstruction.

The reflectometry device and suction controller of the system may be together configured to determine the suction catheter tip is at the obstruction and indicate that suction may begin when the suction catheter tip is determined to be at the obstruction.

The reflectometry device of the system may be configured to analyze timings and amplitudes of the returning acoustic reflections over a plurality of quiet periods to determine an increase in tube resistance and indicate a recommendation of suctioning based on the increase in tube resistance.

The reflectometry device of the system may be configured to send the location and degree of obstruction to a suction controller, wherein the suction controller advances the suction catheter to the obstruction.

The reflectometry device of the system may be configured to measure a duration of suctioning by using at least one microphone to detect suction sounds from the suction tube.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

For purposes of promoting an understanding of the principles of the method and system, reference will now be made to the embodiment illustrated in the drawings, and specific language will be used to describe that embodiment. It will nevertheless be understood that no limitation of the scope of the method and system is intended. Alterations and modifications, and further applications of the principles of the method and system as illustrated therein, as would normally occur to one skilled in the art to which the method and system relates are contemplated, are desired to be protected. Such alternative embodiments require certain adaptations to the embodiments discussed herein that would be obvious to those skilled in the art.

An acoustic reflectometry system's sound waves monitor the artificial airway, alerting clinicians in real time of ETT obstructions or situations that may lead to ETT obstructions. Using principles similar to sonar, the acoustic reflectometry system emits a sound signal into the ETT and records the returning echoes that arise from cross-sectional area discontinuities within the tube and patient airways. The timing and amplitude of these echoes are analyzed by the system to non-invasively estimate the degree and location of obstructions within the ETT and airways. For example, the system analyzes the timing and amplitude of echoes that come from within the ETT to estimate the location and size of obstructions. This may help clinicians identify an obstruction that forms in the endotracheal tube so it can be removed before the patient is harmed. It may also help the clinician differentiate patient biting or tube kinking from lung secretion buildup by noting the reported location of the obstruction.

An acoustic reflectometry system consists of an adapter connected to the proximal end of an ETT and to a monitor. Embedded inside the adapter is a sound generator such as a miniature speaker, for example, and at least one receiver such as a microphone array, for example. With these components, the system employs acoustic reflectometry by emitting sound waves from the speaker into an intubated ETT, detecting the returning acoustic reflections, or echoes, with the microphones, and then examining the echo timings and amplitudes to infer characteristics of the ETT and airway. The system's algorithms analyze the echo signal and provide information about the size of the passageway around the ETT tip, location and size of ETT obstructions, and relative movement of the ETT tip within the trachea.

The microphone array allows the system to determine the direction from which echoes arrive. As a result, the system can selectively filter all echoes that arise from devices on the ventilator side of the adapter, such as closed-circuit suction catheters, Y-connectors, ETCO2 sensors, and filters, for example. This selective filtering allows the system to obtain an echo waveform from the ETT and airways that is free of ventilator circuit echoes.

The human airways are a network of bifurcating branches starting at the trachea and ending at the alveoli—the small sacs where the oxygen and carbon dioxide exchange takes place. An interesting property of the airways is that even though the cross-sectional area of each individual segment decreases as the branching depth increases, the total cross-sectional area (arrived at by adding up the cross-sectional areas of all parallel segments) undergoes a rapid increase after several generations of airway branching. In other words, the airways behave acoustically like a horn with a bell at the end, and sound waves traveling down the airways will be reflected at the bell. The negative pressure wave from this bell-shaped region is used by the system as a reference to which changes in ETT tip position are tracked. The bell begins around the 6th branching generation (approximately 5 cm past the carina in adults).

There is no echo from the carina that can be tracked. Unfortunately, since the additive cross-sectional area of the two main stem bronchi is approximately equal to the trachea's cross-sectional area, there are no echoes of significance that arise from the carina.

While a majority of medical devices that use acoustics operate in the ultrasonic frequency range, the acoustic reflectometry system operates in an audible range below 20 kHz to ensure planar wave behavior within the ETT and airways. Since the sounds typically found in the ventilator circuit—such as respiratory sounds, secretion sounds, or cuff leak sounds—can potentially interfere with the echo signals used by the system, a series of advanced data collection algorithms are used to obtain a clean echo signal during ventilation.

When connected to a patient, the acoustic reflectometry system collects a majority of its measurements during the quiet period of ventilation between end expiration and inspiration. As a result, the acoustic reflectometry system monitor provides updates to the ETT status approximately every patient breath, depending on the level of noise present between breaths. For cases where excessive noise interferes with acoustical measurements such that the ETT status is not updating, the acoustic reflectometry system gives the clinician the option to listen directly to the adapter microphones via the monitor speaker. This assists the clinician in determining the interfering noise source so they can rectify it if possible. Examples of interfering noise sources may include: a leaky ETT cuff, secretions in the airway and/or ETT, a high respiratory rate, a nebulizer, or patient coughing.

Figure 1:
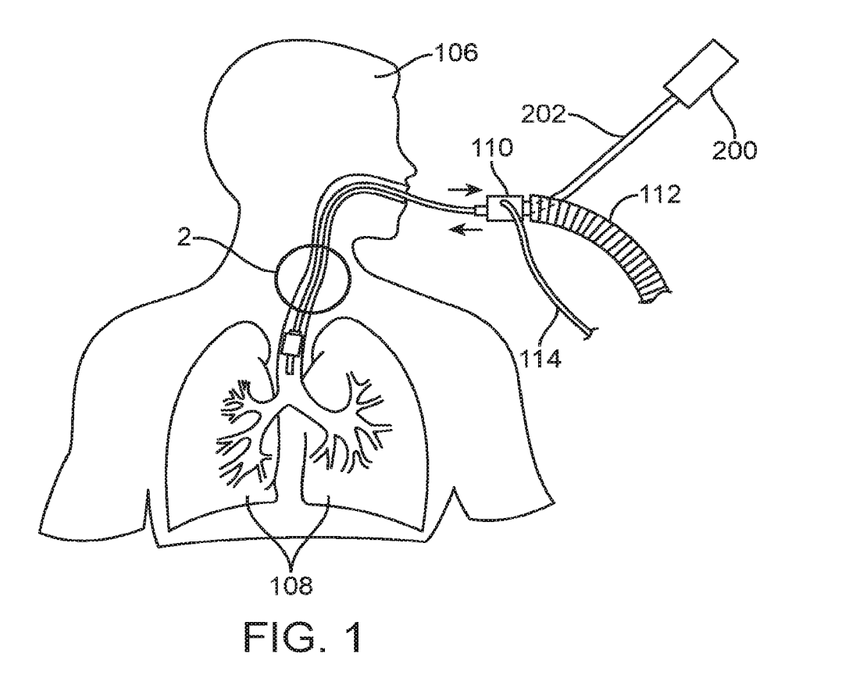
FIG. 1 is a diagrammatical view illustrating proper insertion of an endotracheal tube ("ETT") into a trachea of a human body and a suction catheter inserted into the ETT.
Figure 2:
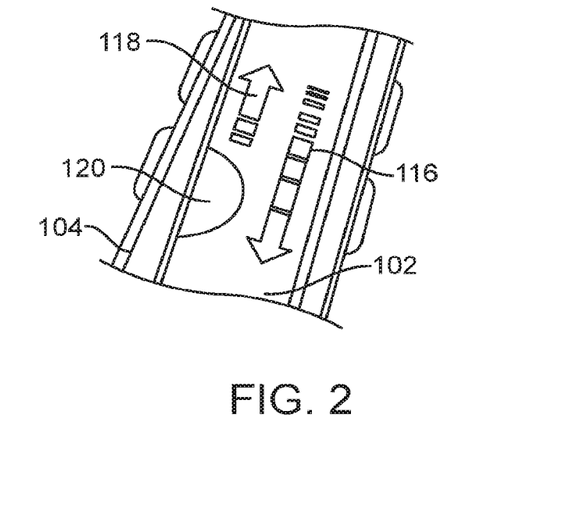
FIG. 2 is a diagrammatical view of sound waves and acoustic reflections traveling within the ETT.

Referring now to the drawings, FIGS. 1 and 2 illustrate proper insertion of an ETT 102 into the trachea 104. For proper mechanical ventilation of the patient 106, it is important that distal end of the ETT 102 is positioned properly within trachea 104 between vocal folds and the carina to provide adequate ventilation to both lungs 108. The acoustic reflectometry system adapter 110 couples in-line between the ETT 102 and the ventilator hose 112 as shown in FIG. 1. The acoustic reflectometry system's sound waves monitor the artificial airway and patient airways, alerting clinicians in real time of situations that may lead to unplanned extubations, ETT obstructions, endobronchial intubation, or esophageal intubation. The adapter 110 is connected by a cord 114 (or wirelessly) to a device 122 (see FIG. 5) to analyze signals from the system. A suction controller 200 and a suction tube 202, which is also referred to as a catheter, are also shown in FIG. 1. The suction controller 200 and suction tube 202 may aid in removing obstructions from the ETT 102. The suction controller 200 may be connected to the device 122.

As shown in FIG. 2, the system uses principles similar to sonar as the acoustic reflectometry system sends a sound signal 116 into the ETT 102 and records the returning echoes 118 that arise from within the tube 102 and patient airways. The timing and amplitude of these echoes 118 are analyzed by the system to detect obstructions 120.

Figure 3:
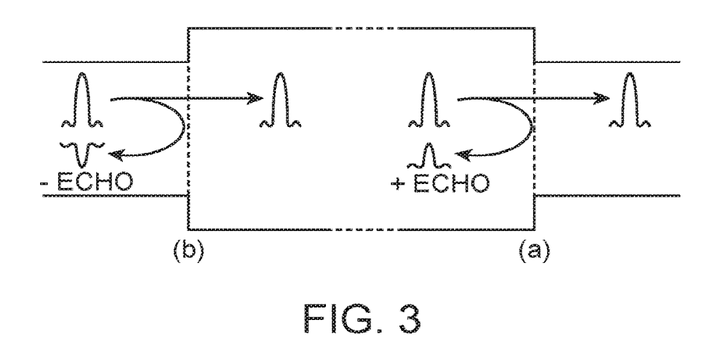
FIG. 3 is a diagrammatical view of the sound waves and respective echo signals (i.e., acoustic reflections) after encountering changes in cross-sectional area in a tube.

Referring now to FIG. 3, as a sound wave travels inside a tube, a fraction of its energy reflects each time it meets with a change in cross-sectional area. If it encounters a decrease in cross-sectional area (see FIG. 3(a)), a positive pressure wave is reflected. This shows up as a positive deflection in the echo signal. If the sound wave encounters an increase in cross-sectional area (see FIG. 3(b)), a negative pressure wave is reflected. This shows up as a negative deflection in the echo signal. The delay time of each echo identifies the distance from the microphone to the changing area that caused the echo. The amplitude of each echo identifies the approximate amount of area change.

Figure 4:
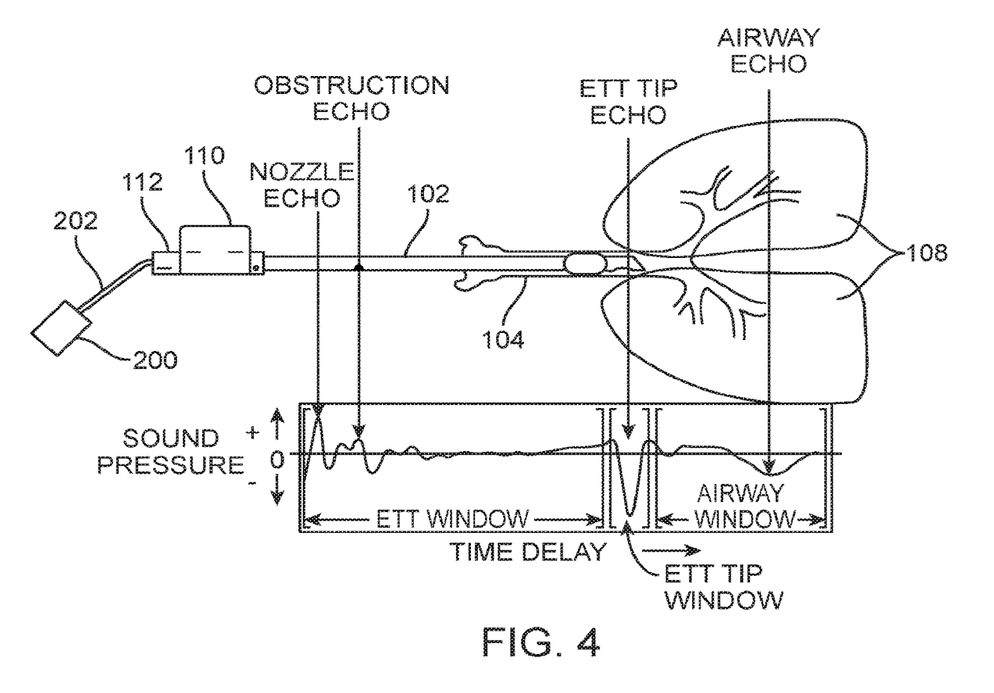
FIG. 4 is a diagrammatical view illustrating relationships between cross-sectional area, amplitude, and time delay of an acoustic reflectometry system inserted into the lower airways.

To illustrate the relationships between cross-sectional area, amplitude, and time delay, FIG. 4 shows an intubated ETT (top) with its corresponding echo signal, as recorded by the acoustic reflectometry system (bottom). The pressure amplitude is represented on Y-axis and the time delay is represented on X-axis. For each deflection in the echo signal, an arrow denotes the corresponding region in the ETT and airways from which that echo arises.

The first echo is a positive deflection (positive pressure) indicating a cross-sectional area decrease. This corresponds to the decrease in the nozzle's diameter from 9 mm to 8 mm. The second echo is a positive deflection immediately followed by a negative deflection, indicating a cross-sectional area decrease and then an increase. This echo could be from a small obstruction in the ETT, from a kink in the ETT, or from a patient biting on the ETT. If the echo amplitude were larger, this would correspond to a larger obstruction (a larger constriction of the ETT lumen). The acoustic reflectometry system estimates the obstruction size from the echo amplitude and the obstruction location from the echo delay time.

The third echo is a negative deflection indicating a cross-sectional area increase. This echo, referred to as the ETT tip echo, is analyzed by the acoustic reflectometry system to estimate the passageway size (or effective diameter) around the ETT. A negative deflection echo indicates that the ETT is located in a passageway that has a larger cross-sectional area than the ETT. This would be the case for an ETT that is in the trachea. If this echo were to change to a positive deflection, it would indicate that the ETT is located in a passageway that has a smaller cross-sectional area than the ETT. This may correspond to an ETT that is in the esophagus or bronchus or that it is clogged at the tip, for example, from mucus.

The last echo, referred to as the airway echo, arises from the bell shaped region in the lower airways. The acoustic reflectometry system tracks the time delay of this airway echo, estimating relative changes in the distance between the ETT tip and the airway echo region. For example, if the time delay between the ETT tip echo and the airway echo is decreasing (airway echo moving to the left), then this indicates that the ETT tip is getting closer to the airway echo region or that the ETT is migrating down the trachea.

Figure 5:
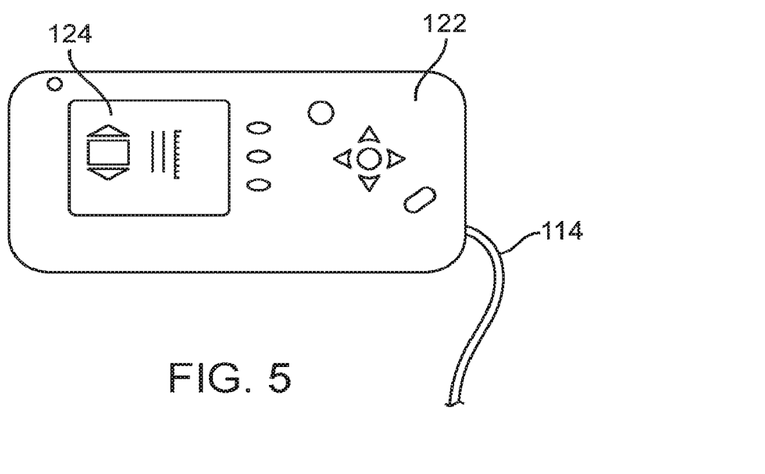
FIG. 5 is a diagrammatical view of a device of the system having a display, a processor and a memory that is accessible to the processor.
Figure 6:
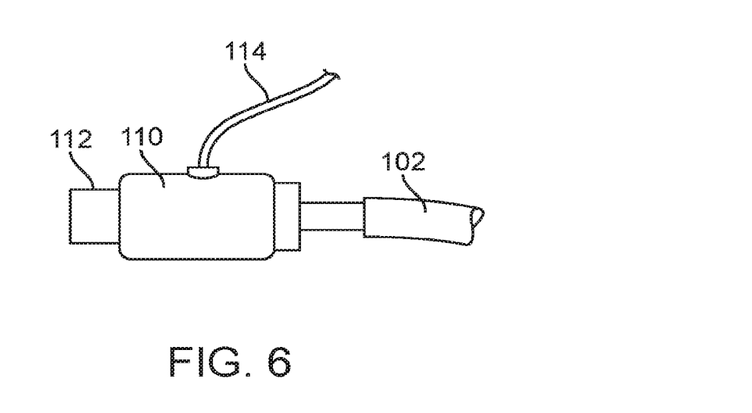
FIG. 6 is a diagrammatical view of an adapter of the system that inserts into the breathing circuit between the ventilator hose and the ETT.

Referring now to FIGS. 5 and 6, the acoustic reflectometry system includes a device 122 that is a handheld, portable device with a display 124 that provides information about the endotracheal tube position, obstruction, and movement. The device 122 has at least one processor and a memory that is accessible to the processor and may store instructions that when executed by the processor cause the system to carry out any of the steps or processes described herein. The device 122 may include circuitry for sending, receiving and processing audio signals from the acoustic reflectometry system adapter 110 via cable 114. As explained below, the acoustic reflectometry system interprets the signals received from the patient's airway and provides feedback to the clinician through intuitive text and graphics. The device 122 may also include circuitry for sending, receiving and processing signals to or from the suction system 200.

Many improvements may be made in the operation of ventilators and other devices by obtaining information that may be gleaned from airway monitoring devices such as the acoustic reflectometry system disclosed herein and using this data and new algorithm to improve prior art ventilator functionality as described below.

Determining Trachea Pressure and Tube Resistance

The pressure within the trachea can be calculated by a ventilator as follows:

$$P_{TRACHEA} = P_{AW} - \Delta P_{TUBE}$$

$$\Delta P_{TUBE} = R_{TUBE} \times \text{Flow}$$

where $P_{TRACHEA}$ is the estimated tracheal pressure, $P_{AW}$ is the measured mean airway pressure at the Y-piece, $\Delta P_{TUBE}$ is the estimated pressure drop across ETT, $R_{TUBE}$ is the estimated ETT resistance (pressure differential across tube), and Flow is the measured airway flow.

Obstructions within the ETT may present a significant obstacle to the flow of air through the tube. The estimated ETT resistance may therefore be improved by using ETT monitoring data that can detect obstructions within the ETT, thereby allowing the calculation of tube resistance as a function the ETT internal diameter and the size and location of one or more obstructions within the ETT. Those skilled in the art will recognize that the acoustic reflectometry system can detect the whole obstruction profile within the ETT from the proximal end to the distal end and an effective tube diameter can be calculated based upon this data. The more accurate tube diameter measurement will allow for a more accurate estimate of the ETT tube resistance, and hence a more accurate estimate of trachea pressure.

The acoustic reflectometry system can monitor the ETT resistance and the presence of obstructions within the ETT over time and, based on an increase in ETT resistance or the presence of obstructions within the ETT, or both, may indicate that the ETT should be suctioned to clear obstructions. The indication may be, for example, a visual or audio indication, such as a flashing light or alarm.

Secretion Management

A recommendation for suctioning the ETT can be generated based upon the value and optionally the trend of the artificial airway resistance as measured by the acoustic reflectometry system.

Figure 7A:
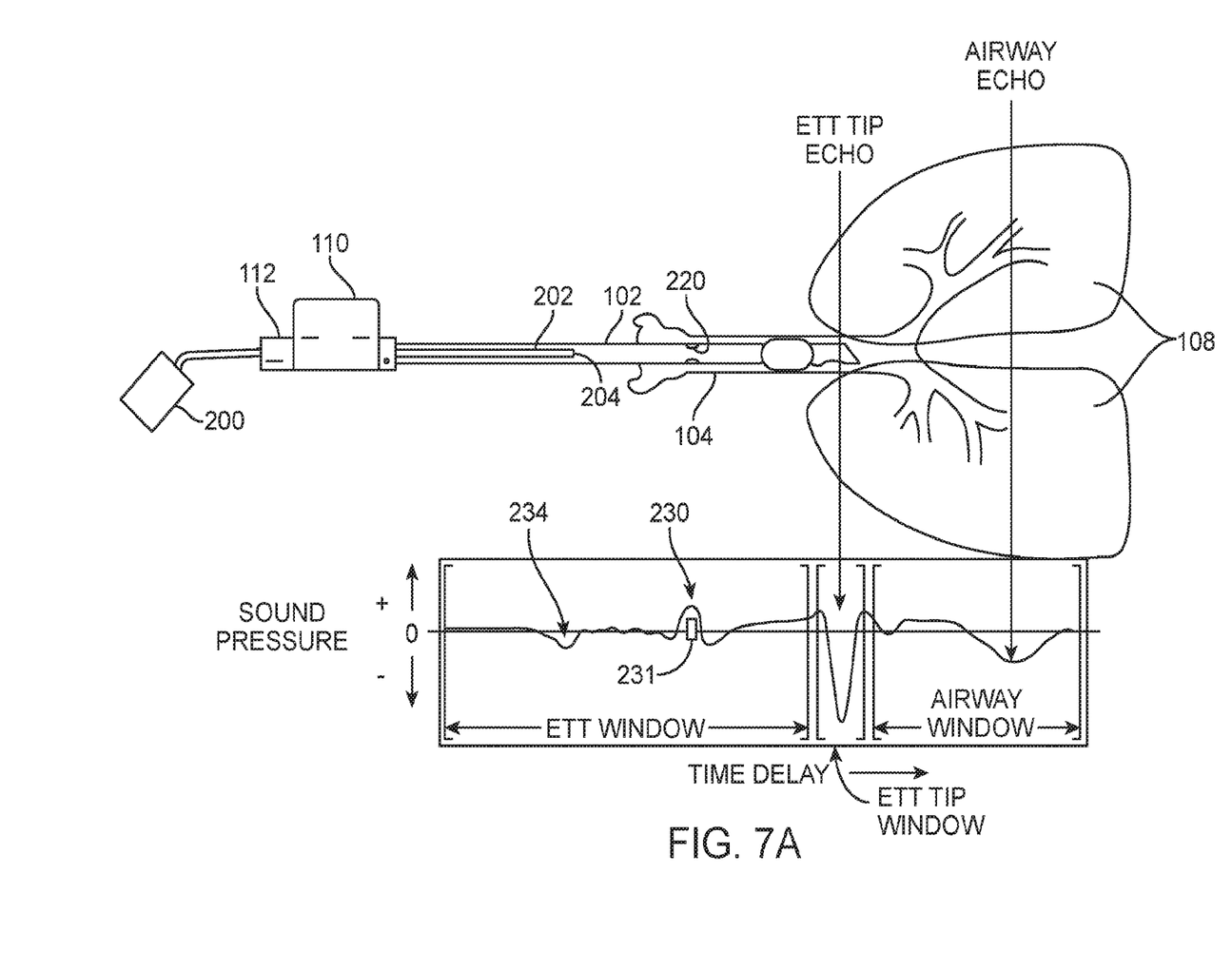
FIG. 7A is a diagrammatical view illustrating an obstruction and a suction catheter in a tube of an acoustic reflectometry system.

The acoustic measurement device may also provide feedback regarding the state of the ETT obstruction and the suction process to aid a medical professional during the suction process or to automate the suction process. For example, FIGS. 7a, 7b, 8a, 8b, 9a, and 9b, depict a process and system for clearing ETT obstructions using suction. The upper portion of FIGS. 7a, 8a, and 9a show a diagram of an airway, including the trachea 104 and lungs 108 along with portions of an acoustic reflectometry system, including an ETT 102, an adapter 110, and a ventilator hose connector 112 that may be connected to a ventilator, and a suction system, including a suction tube 202 that is inserted within the ETT and a suction controller 200. The system shown in FIGS. 7a, 7b, 8a, 8b, 9a, and 9b, may be used for both automated and manual suctioning of obstructions, as discussed herein.

The suction controller 200 may include valves, motors, positioning measuring devices and other means for controlling the insertion and retraction of the suction tube 202 from the ETT and the volume and pressure of suction provided by the suction tube. For example, the suction controller 200 may include an encoder and actuator for inserting the suction tube into the ETT and measuring the insertion distance of the tube in the ETT. The suction controller 200 may also include valves or pressure regulators to turn the suction flow to the suction tube on and off and to regulate the suction pressure. In some embodiments, the valves or pressure regulators may fluidically couple and decouple the suction tube to a suction source or vacuum source, such as a vacuum pump or vacuum lines within a hospital room.

The bottom portion of FIGS. 7a, 8a, and 9a show a display of the echo waveform arising from within the ETT and patient airway over time. The display may include an indication of the locations of the echoes within the ETT and patient airway. For example, the display shown in FIGS. 7a, 8a, and 9a, include a ETT window showing the echo from the ETT, a ETT tip window showing the echo at or proximate the ETT tip, and an airway window that shows the echo from the airway.

When the suction tube 202 is inside the ETT and the suction tube has an external diameter approaching the internal diameter of the ETT, the space between the suction tube and ETT will be characterized by a small cross-sectional area and large surface area. Compared to the sound attenuation within the ETT without the suction tube, this configuration may result in a significant increase in sound attenuation for sound waves propagating alongside the suction tube within the ETT. To compensate for this increased sound attenuation, an attenuation compensation scaling factor, such as time gain compensation, may be applied to each sample within the digitized echo signal to remove the effects of the sound attenuation.

Referring now to FIG. 7A, an obstruction 220 is shown in the ETT 102. A positive echo 230 in the ETT window of the display indicates the location and degree of the obstruction 220. The location, such as the distance within the ETT, and the degree of obstruction, such as percent of the ETT obstructed or the equivalent diameter of the ETT at the obstruction, may also be indicated numerically on a display, such as depicted at the bottom of FIG. 7A. A negative echo 234 in the ETT window of the display indicates the location of the suction tip 204 within the ETT. The location, such as the distance within the ETT may also be indicated numerically. The obstruction 220 may also be indicated on the display with a display object, such as an icon. For example, a rectangular icon 231 graphically represents the location of the obstruction 220.

Figure 7B:
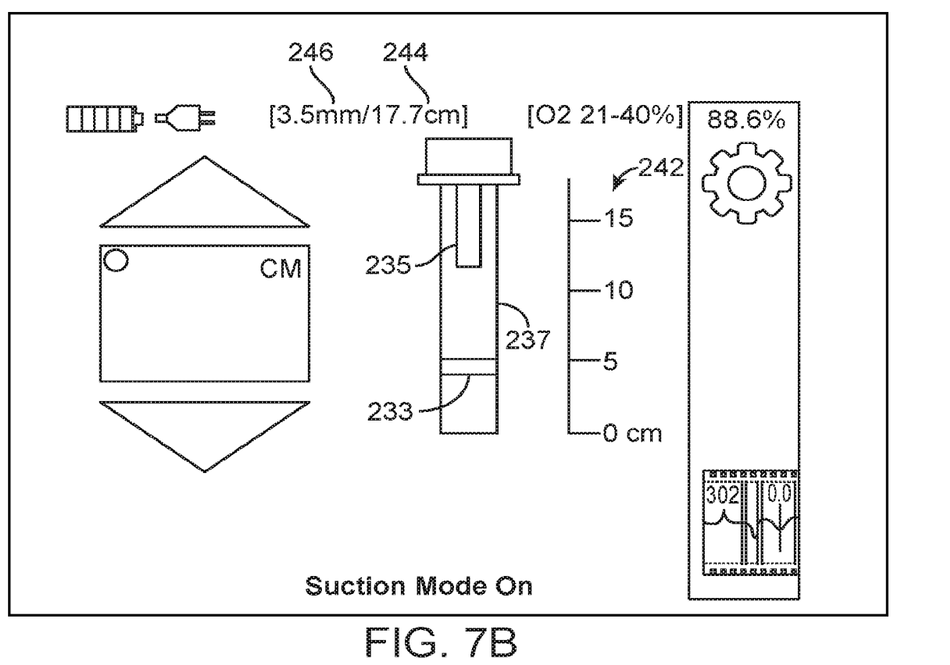
FIG. 7B is an illustration of a display showing an obstruction and a suction catheter in an tube according to one or more embodiments herein.
Figure 8A:
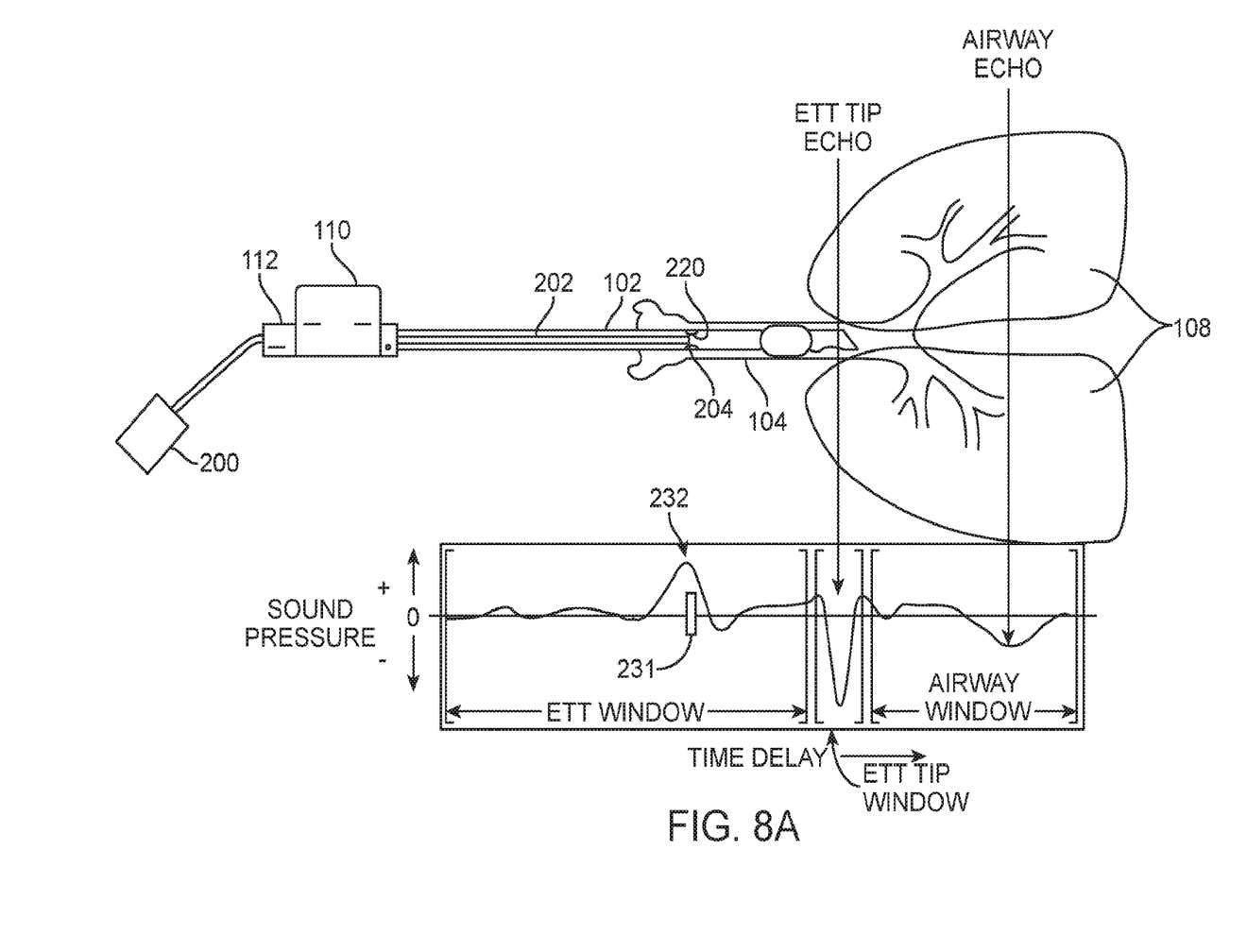
FIG. 8A is a diagrammatical view illustrating suction of an obstruction in a tube of an acoustic reflectometry system.

The acoustic reflectometry system may also include an alternate or additional display, such as the display shown in FIG. 7B. This display includes a graphical representation 237 of the ETT 102, along with a graphical representation 235 of the suction tube 202 and a graphical representation 233 of the obstruction 220. The display may also include objects such as a distance scale 242 along the length of the ETT 233 to aid in communicating the relative positions of the ETT 102, suction tube 202, and obstruction 220. The display may also include other features, such as an indication of ETT internal diameter 246 and ETT length 244.

In some embodiments, the location and degree of the obstruction 220 in the ETT 102 and the location of the suction tube tip 204 may be determined by the acoustic reflectometry system and sent to the suction system 200 for use in guiding the suction tube 202 and controlling the suction process. In some embodiments, the location and degree of the obstruction is determined simultaneously with the location of the suction tube and/or suction tube tip.

For example, in an automated process, the acoustic reflectometry system may determine the location and degree of the obstruction 220 and then send the location and degree of the obstruction 220 to the suction controller 200 which may advance the suction tube 202 into the ETT 102 until the suction tube tip 204 is at the obstruction 220, as shown in FIG. 8A.

In some embodiments, the acoustic reflectometry system indicates the location and degree of the obstruction 220 on the display. A medical processional may refer to such an indication when performing manual suctioning, for example as they insert the suction tube into the ETT 102 and approach the obstruction 220.

FIG. 8A shows the system at a stage in the suctioning process wherein the suction tube tip 204 is at the location of the obstruction 220. The acoustic reflectometry system may indicate that the suction tube tip 204 is at the location of the obstruction with an increased positive echo 232, rather than a negative echo followed by a positive echo, as shown in FIG. 7A. This occurs because, when the suction tube tip 204 is at the location of the obstruction, the tube tip 204 and obstruction 220 appear as a larger obstruction. In some embodiments, the tube tip 204 and the obstruction 220 may be such that the entire ETT is obstructed when the tube tip 204 is at the obstruction 220. In such embodiments, the echo my include a large positive echo at the location of the obstruction 220 and tube tip 204. The obstruction 220 may also be indicated with an icon, such as the obstruction icon 231.

Figure 8B:
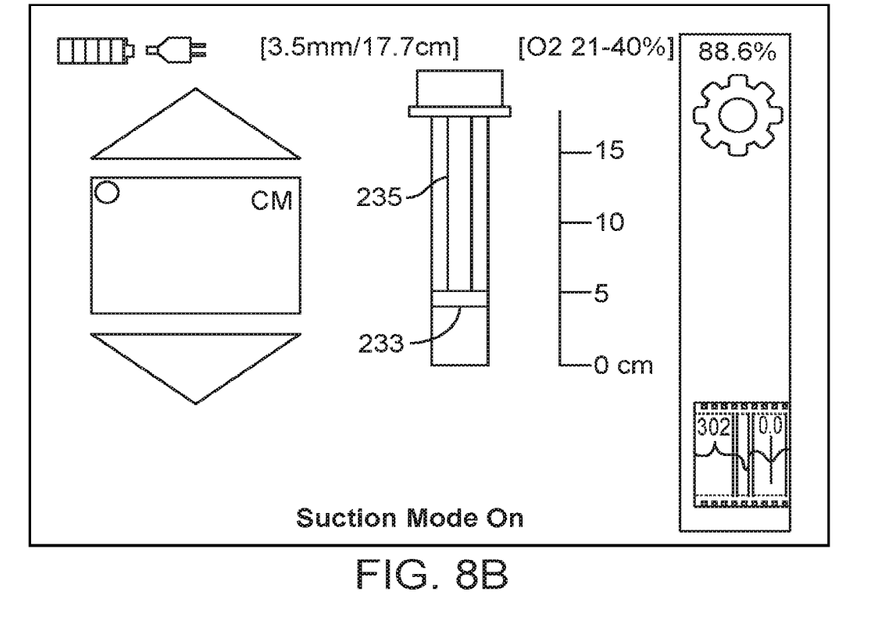
FIG. 8B is an illustration of a display showing the suction of an obstruction and a suction catheter in a tube of an acoustic reflectometry system according to one or more embodiments herein.
Figure 9A:
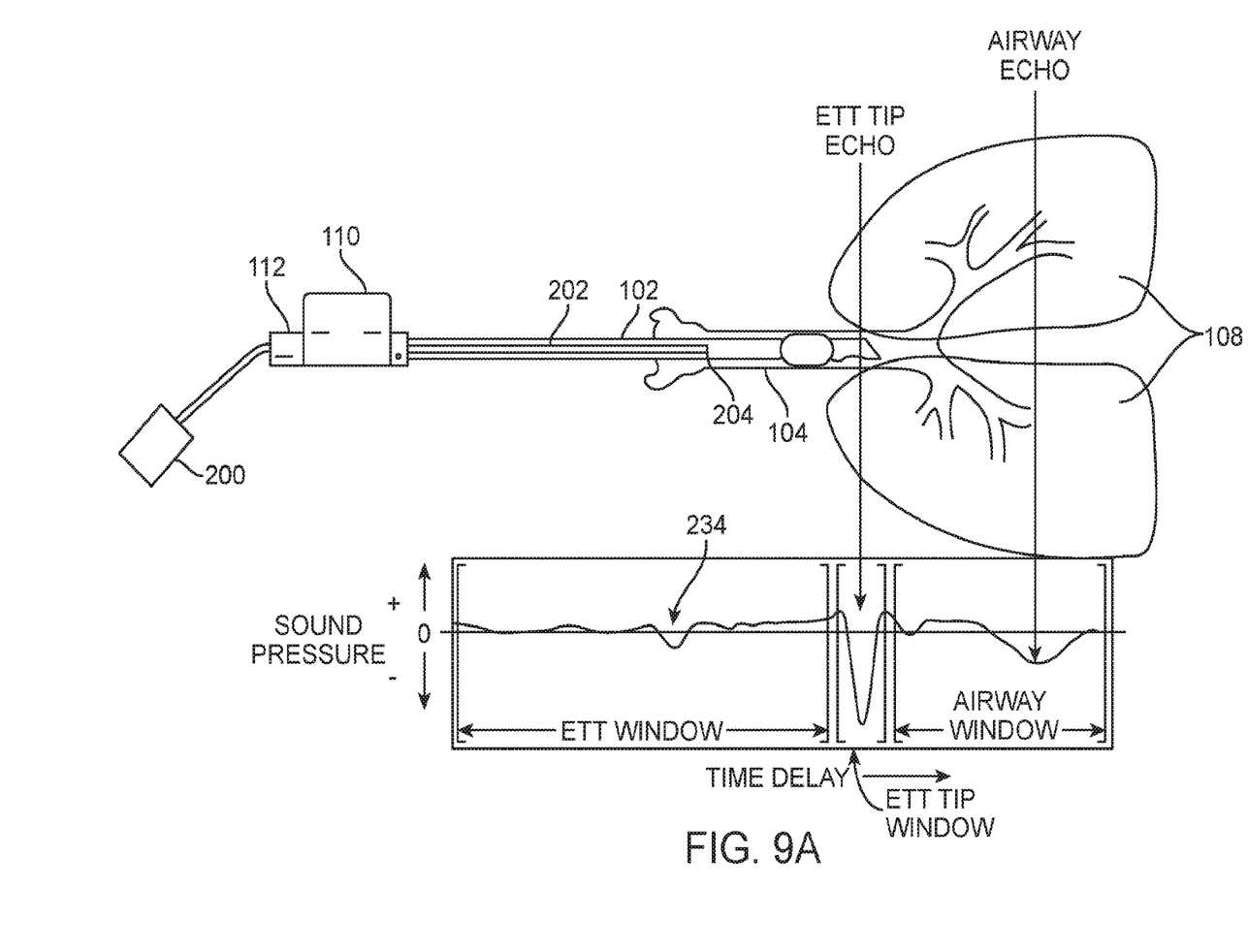
FIG. 9A is a diagrammatical view illustrating a suction catheter within an unobstructed tube of an acoustic reflectometry system.

The acoustic reflectometry system may also show the positions of the suction tube 202 and obstruction 220 on an additional or alternative display, such as that shown in FIG. 8B. At this stage of the suction process, the graphical representation 235 of the suction tube 202 is at the location of the graphical representation 233 of the obstruction 220, indicating that the tip 204 of suction tube 202 is at the location of the obstruction 220.

When the acoustic reflectometry system indicates that the suction tube tip 204 is at the obstruction, the system may indicate that suction should begin. For example, in a manual process, the display may include an indication that suction should begin, at which point the medical processional may apply suction pressure and flow to the suction tube 202 which may suck the obstruction out of the ETT. In some embodiments, the acoustic reflectometry system may output a signal to the suction system 200. In response to the signal, the suction system 200 may couple the suction tube 202 to a suction or vacuum source to suck the obstruction out of the ETT, such as by actuating a valve or pressure regulator.

At the end of a first suctioning attempt, the suction tube 202 may be decoupled from the vacuum or suction source and then withdrawn or partially withdrawn from the ETT, for example, as shown in FIG. 9A.

FIG. 9A shows the system at a stage in the suctioning process wherein the suction tube tip 204 is withdrawn from the previous location of the now removed obstruction 220. With the suction tube tip 204 partially withdrawn from the previous location of the obstruction 220, the acoustic reflectometry device may show the status of the ETT and any obstructions therein. For example, as shown in FIG. 9A, the display shows a negative echo 234 that indicates the location of the suction tube tip 204. If the acoustic reflectometry device indicates that an obstruction is still present or moved, for example as shown in FIG. 7A, then the suction tube 202 may be advanced into the ETT 102 to the location of the obstruction and the suction process may be repeated.

Figure 9B:
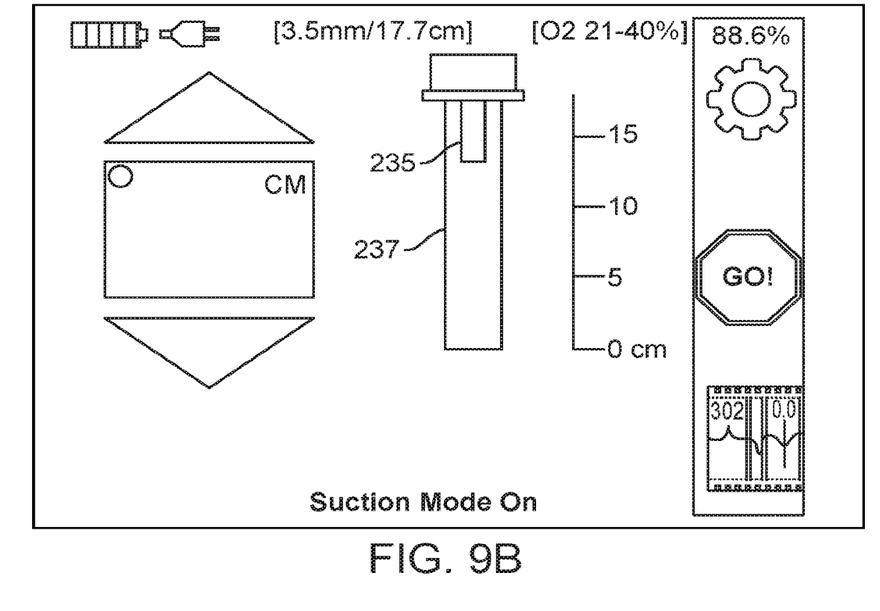
FIG. 9B is an illustration of a display showing a suction catheter within the unobstructed tube of an acoustic reflectometry system according to one or more embodiments herein.

When the acoustic reflectometry device indicates that the obstruction 220 is adequately removed, for example as shown in FIG. 9A, then the suction tube 202 may be withdrawn from the ETT. The acoustic reflectometry device may also evaluate suction performance based on an estimated ETT resistance that may be determined from the location and size of the remaining obstruction. The alternative or additional display shown in FIG. 9B shows a graphical representation of the suction tube 235 and a graphical representation 237 of the unobstructed ETT 102.

In some embodiments, if the suctioning has reduced the obstruction such that the estimated resistance of the ETT is below a threshold, then the acoustic reflectometry device may indicate that suction has been adequately performed and can stop. In some embodiments, the suction controller 200 may retract the suction tube 202 from the ETT. In some embodiments, the medical professional may manually withdraw the suction tube 202 from the ETT.

After withdrawal of the suction tube 202 from the ETT, the acoustic reflectometry device may continue to monitor the airway for proper breathing function and the ETT for obstructions.

In some embodiments, the acoustic measurement device, with or without coordination with a ventilator, may take pre-suctioning and post-suctioning measurements for tube resistance which may be analyzed and used as a basis for a message that indicates that the suctioning effort was successful or not completely successful. This, in turn, could alert the caregiver, such as a medical professional, to dried secretions that are not removed by regular suctioning and might be an indication for ETT replacement, increased humidification, or other interventions such as use of a "tube rescue" device which scrapes mucus debris from walls of the ETT lumen.

In some embodiments, the acoustic reflectometry device times how long the caregiver applied suction to the ETT during a single pass of the suction tube 202. The suction time may be determined by using at least one microphone within the adapter 110 to detect the suction sounds from the suction tube tip 204 and using a timer within the device 122 to time the suctioning duration. The device 122 may report the running timer value in seconds on the device display 124 during suctioning. This timer may be used to train medical professionals to apply suctioning for an adequate duration to help improve the effectiveness of suctioning.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for guiding suction of an obstruction, the method comprising:
   emitting sound waves from a sound generator into a tube, inserted into a body, having a suction catheter positioned within the tube;
   detecting returning acoustic reflections with at least one sound receiver;

analyzing, using a processor, the returning acoustic reflections to determine a location of an obstruction within the tube and a location of a tip of the suction catheter within the tube; and displaying a representation of the location of the tip of the suction catheter and a representation of the location of the obstruction within the tube based on the determined location of the tip of the suction catheter and the determined location of the obstruction.

2. The method of claim 1, further comprising:
sending, via the processor, the location of the obstruction to a suction controller coupled to the suction catheter; and
advancing, via the suction controller, the suction catheter to the obstruction.

3. The method of claim 1, further comprising:
determining, using the processor, that the tip of the suction catheter is at the location of the obstruction; and
providing an output to recommend that suction begin in response to determining that the tip of the suction catheter is at the obstruction.

4. The method of claim 1, further comprising:
analyzing, using the processor, the returning acoustic reflections to determine an increase in tube resistance; and
providing a recommendation of suctioning based on the increase in tube resistance.

5. The method of claim 1, further comprising:
detecting, using the at least one sound receiver, suction sounds from the suction catheter; and
determining, using the processor, a duration of suctioning based on the suction sounds.

6. The method of claim 1, wherein the tube comprises an endotracheal tube.

7. The method of claim 1, wherein the representation of the location of the tip of the suction catheter and the representation of the location of the obstruction are displayed concurrently.

8. The method of claim 1, further comprising:
determining, using the processor, that the obstruction has been removed from the tube; and
removing, from display, the representation of the obstruction in response to determining that the obstruction has been removed from the tube.

9. A system for guiding suction of an obstruction, the system comprising:
a sound generator to emit sound waves into a tube, inserted into a body, having a suction catheter positioned within the tube;
at least one sound receiver to detect returning acoustic reflections;
a processor and a memory that is accessible to the processor and stores instructions that, when executed by the processor, cause the processor to perform operations comprising:
analyzing timings and amplitudes of the returning acoustic reflections to determine a location of an obstruction within the tube and a location of a tip of the suction catheter within the tube; and
causing a display of a representation of the location of the tip of the suction catheter and a representation of the location of the obstruction within the tube based on the determined location of the tip of the suction catheter and the determined location of the obstruction.

10. The system of claim 9, wherein the operations further comprise:

determining that the tip of the suction catheter is at the obstruction based on the analysis of the returning acoustic reflections; and
instructing the display to update the representation of the tip of the suction catheter within the tube to show the tip of the suction catheter at the obstruction.

11. The system of claim 9, wherein the operations further comprise sending the location of the obstruction to a suction controller coupled to the suction catheter.

12. The system of claim 9, wherein the representation of the tip of the suction catheter within the tube comprises a graphical representation with a first shape that represents the tip of the suction catheter and a second shape that represents the tube.

13. The system of claim 12, wherein the representation of the obstruction is part of the graphical representation with a third shape that represents the obstruction.

14. The system of claim 9, wherein the operations further comprise:
analyzing, using the processor, the timings and the amplitudes of the returning acoustic reflections to monitor the location of the tip of the suction catheter as the tip of the suction catheter moves within the tube; and
updating the representation of the tip of the suction catheter within the tube as the tip of the suction catheter moves within the tube.

15. The system of claim 9, wherein the tube is an endotracheal tube.

16. A system for guiding suction of an obstruction, the system comprising:
an endotracheal tube;
a suction catheter positioned in the endotracheal tube;
a display;
an adapter connected to the endotracheal tube, the adapter comprising:
a sound generator to emit sound waves into the endotracheal tube having the suction catheter positioned within the endotracheal tube;
at least one sound receiver to detect returning acoustic reflections; and
a processor and a memory that is accessible to the processor and stores instructions that, when executed by the processor, causes the system to perform operations comprising:
analyzing timings and amplitudes of the returning acoustic reflections to determine a location of an obstruction within the endotracheal tube and a location of a tip of the suction catheter within the endotracheal tube;
displaying, on the display, a representation of the location of the tip of the suction catheter based on the determined location of the tip of the suction catheter; and
displaying, on the display, a representation of the location of the obstruction within the endotracheal tube based on the determined location of the obstruction.

17. The system of claim 16, further comprising a suction controller coupled to the suction catheter and wherein the operations further comprise:
sending the location of the obstruction to the suction controller coupled to the suction catheter; and
advancing, via the suction controller, the suction catheter to the obstruction.

18. The system of claim 17, wherein the operations further comprise:

determining that the tip of the suction catheter is at the obstruction; and displaying, on the display, an output to recommend that suction begin in response to determining that the tip of the suction catheter is at the obstruction.

19. The system of claim 16, wherein the operations further comprise:

analyzing the returning acoustic reflections to determine an increase in tube resistance; and displaying, on the display, a recommendation of suctioning based on the increase in tube resistance.

20. The system of claim 16, wherein the operations further comprise:

detecting, using the at least one sound receiver, suction sounds from the suction catheter;

determining a duration of suctioning based on the suction sounds; and displaying, on the display, an indicator of the determined duration.

* * * * *